United States Patent [19]
Fogler, Jr. et al.

[11] Patent Number: 5,195,700
[45] Date of Patent: Mar. 23, 1993

[54] LOW SPEED MODEL FOLLOWING VELOCITY COMMAND SYSTEM FOR ROTARY WING AIRCRAFT

[75] Inventors: Donald L. Fogler, Jr., Milford; James L. Richard, Stratford; Phillip J. Gold, Shelton, all of Conn.; Steven L. Glusman, Springfield, Pa.

[73] Assignee: United Technologies Corporation, Hartford, Conn.

[21] Appl. No.: 751,437

[22] Filed: Aug. 28, 1991

[51] Int. Cl.⁵ .................. B64C 11/44; G05D 1/10; G05D 1/08
[52] U.S. Cl. ............... 244/17.21; 244/17.13; 244/177; 244/181; 244/76 R; 364/434
[58] Field of Search ............ 244/17.13, 17.21, 177, 244/180, 181, 191, 193, 76 R; 364/432, 433, 434, 435

[56] References Cited
U.S. PATENT DOCUMENTS

| | | |
|---|---|---|
| 3,057,584 | 10/1962 | Bretoi ............................... 244/193 |
| 4,004,756 | 1/1977 | Gerstine et al. .................. 244/17.13 |
| 4,106,094 | 8/1978 | Land ...................................... 364/434 |
| 4,371,937 | 2/1983 | Adams et al. ....................... 364/434 |
| 4,371,938 | 2/1983 | Wright et al. ...................... 364/434 |
| 4,420,808 | 12/1983 | Diamond et al. .................. 364/434 |
| 4,527,242 | 7/1985 | McElreath et al. ................ 364/432 |
| 4,573,125 | 2/1986 | Koenig .................................. 364/434 |
| 4,642,774 | 2/1987 | Centala et al. ..................... 364/434 |
| 4,697,768 | 10/1987 | Klein ..................................... 364/434 |
| 5,008,825 | 4/1991 | Nadkarni et al. ................... 364/434 |

Primary Examiner—Joseph F. Peters, Jr.
Assistant Examiner—Virna Lissi Ansley
Attorney, Agent, or Firm—Patrick J. O'Shea

[57] ABSTRACT

A helicopter flight control system (21) includes a model following control system architecture which operates in a velocity command mode at low ground speeds. The control system processes information from a variety of helicopter sensors (31) in order to provide a command signal to the main rotor (11) of the helicopter which results in a ground speed which is proportional to the input provided via a sidearm controller (29).

10 Claims, 8 Drawing Sheets

LOW SPEED MODEL FOLLOWING VELOCITY COMMAND SYSTEM FOR ROTARY WING AIRCRAFT

The has government has rights to this invention pursuant to a contract awarded by the Department of the Army.

DESCRIPTION

1. Technical Field

This invention relates to flight control systems for rotary wing aircraft, and more particularly to control systems with model following control laws that operate in a velocity command mode.

2. Background Art

It is well known that manual control of a rotary winged aircraft in hover is a difficult maneuver for a pilot due to the high workload involved, and the inherent difficulty of maintaining a fixed position over the ground. These problems escalate in an attack helicopter performing bob-up maneuvers from below tree line level for target acquisition and designation. Such a maneuver requires precision control of aircraft position and velocity especially when operating in a degraded visual environment.

In typical rotary winged aircraft flight control systems, pilot inputs are used to set a main rotor blade tip path which results in a certain aircraft attitude, and velocity vector (i.e., a flight path). However such a control system leads to the aforementioned high workload the pilot experiences while hovering in degraded visual environments. With such a flight control system if the pilot is hovering above a particular spot and desires to move the aircraft to another location and hover, he inputs a lateral cyclic input which starts the aircraft moving towards the new hover location. As the aircraft approaches the new desired hover location, the pilot provides an arresting cyclic input to bring the aircraft to a stop over the new desired hover location. Such a positioning system results in a high workload being placed on the pilot since he may have to iterate several times before being able to enter a hover over the new desired location. Furthermore, the difficulty of entering hover over a precise location is increased under degraded visual flight conditions in which an attack helicopter must be fully capable of operating.

Automatic systems (e.g., autopilot systems) have been developed which allow a pilot to program the system to fly to a predetermined location and enter a hover over that predetermined location. However, problems occur when the aircraft is under manual pilot control (i.e., a combat situation involving below tree line aircraft operations) which requires a great deal of pilot work load in order to manually control the aircraft attitude and hence position of the aircraft at low airspeeds.

DISCLOSURE OF THE INVENTION

An object of the present invention is to reduce the amount of pilot work load required to manually fly a rotary winged aircraft at low airspeeds.

Another object of the present invention is to allow small precise changes to aircraft position with low pilot workload.

Another object of the present invention is to provide an aircraft flight control system which operates a velocity command model in response to pilot inputs at low airspeeds.

Yet another object of the present invention is to generate aircraft commands necessary to provide a ground referenced velocity response which is proportional to lateral or longitudinal inputs on a sidearm controller.

A further object of the present invention is to provide a rotary winged aircraft flight control system which transitions smoothly in and out of the velocity command mode.

According to the present invention, a model following flight control system for a rotary winged aircraft operates in a velocity command mode at low airspeeds to control aircraft velocity in response to pitch and roll stick commands from the pilot.

The present invention allows a rotary winged aircraft pilot to make precise changes to an aircraft's position while the aircraft is operating at low airspeeds, thereby reducing the pilot workload required to make such a precise change.

These and other objects, features and advantages of the present invention will become more apparent in light of the following detailed description of a best mode embodiment thereof as illustrated in the accompanying drawings.

BEST MODE FOR CARRYING OUT THE INVENTION

Figure 1:
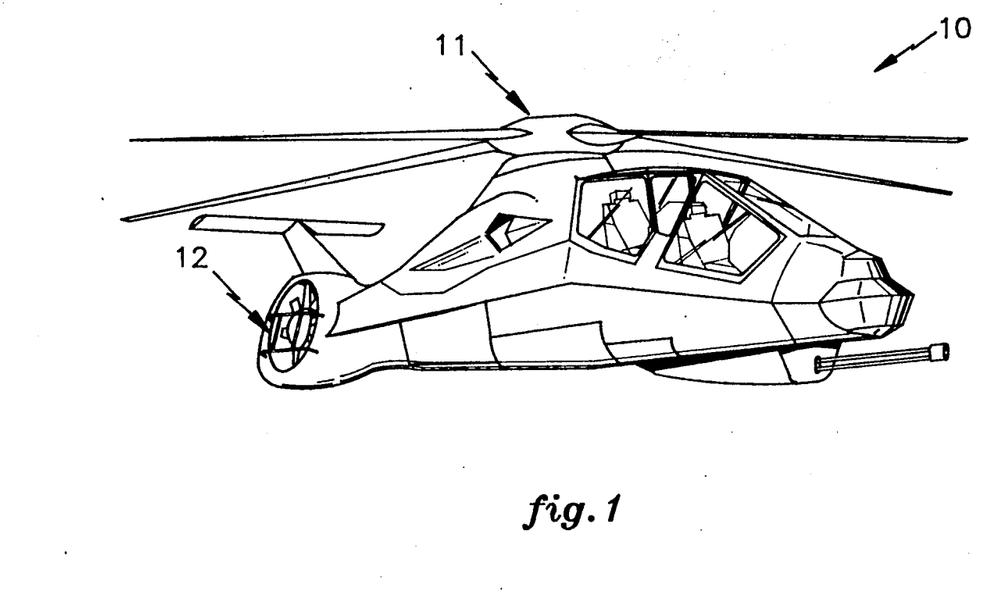
FIG. 1 is a pictorial illustration of a rotary winged aircraft in which the present invention may be used.

Referring first to FIG. 1, which is a pictorial illustration of a helicopter embodiment 10 of a rotary winged aircraft in which the present invention may be used. The helicopter includes a main rotor assembly 11 and tail rotor assembly 12.

Figure 2:
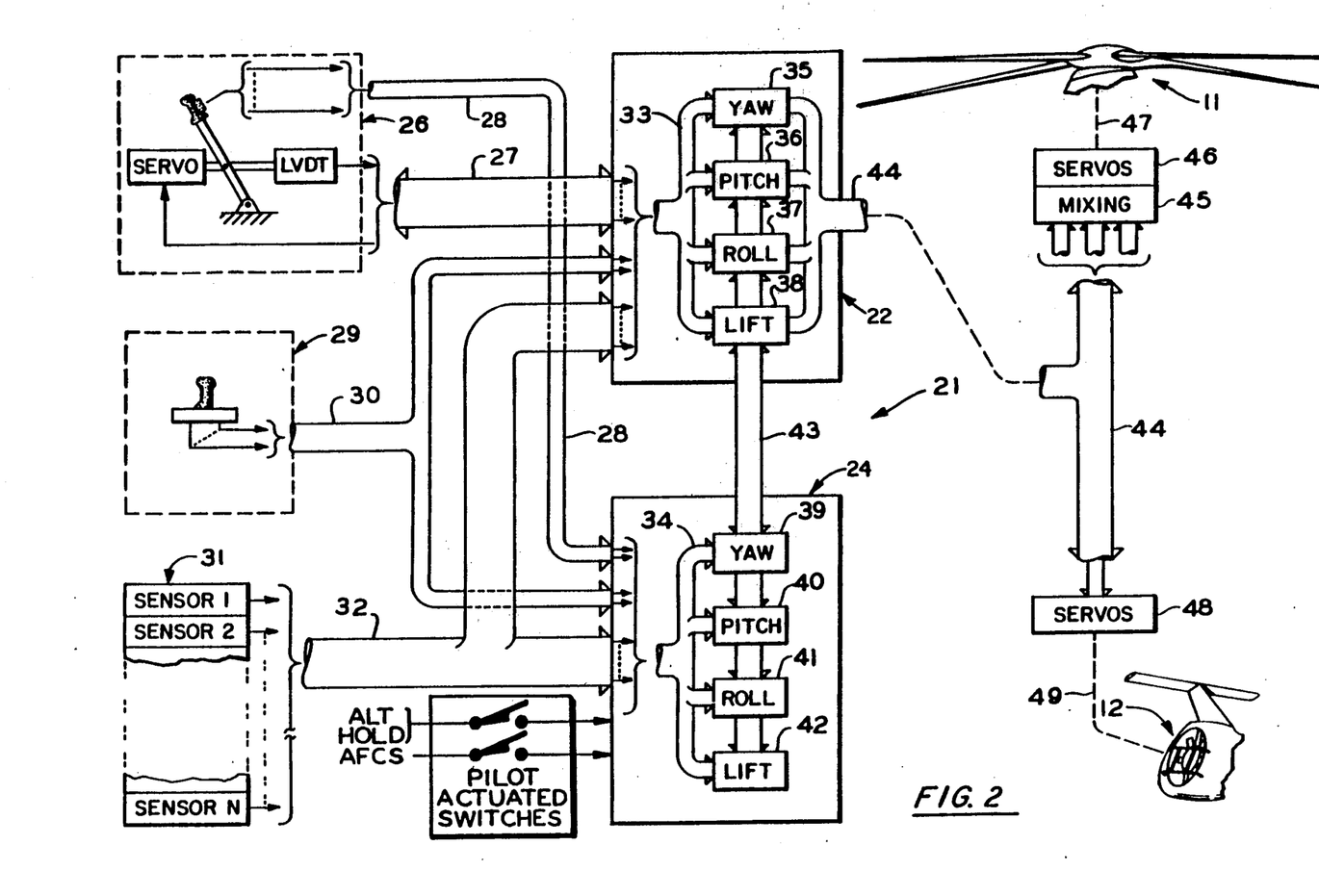
FIG. 2 is a block diagram of the model following flight control system of the present invention.

Referring now to FIG. 2, the helicopter flight control system of the present invention 21 is a model following control system which shapes the pilot's sidearm controller and displacement stick commands through an "inverse vehicle model" to produce a desired aircraft response. The system includes a Primary Flight Control System (PFCS) 22 and an Automatic Flight Control System (AFCS) 24. The PFCS receives displacement command output signals from a displacement collective stick 26 on line 27 and the AFCS receives the collective stick discrete output signals on a line 28. The PFCS and AFCS each receive the force output command signals of a force type four axis sidearm controller 29, on lines 30, and the aircraft's sensed parameter signals from sensors 31, on lines 32. The pilot command signals on lines 27, 28, and 30 and the sensed parameter signals on lines 32 are shown consolidated within trunk lines 33 and 34 in the PFCS and AFCS, respectively.

The PFCS and AFCS each contain control channel logic for controlling the yaw, pitch, roll and lift axes of the aircraft. In FIG. 2 these logic modules are shown by blocks 35-38 for the PFCS and blocks 39-42 for the AFCS. The PFCS provides rotor command signals and the AFCS logic provides conditioning and/or trimming of the PFCS four axis logic functions. The PFCS and AFCS logic modules interconnect through bus 43.

As described in detail hereinafter, the PFCS and AFCS use a model following algorithm in each control axis to provide rotor command signals on output lines 44 to a main rotor mixing function 45 which commands displacement of mechanical servos 46 and linkages 47 to control the tip path plane of the main rotor 11. Command signals are also provided on lines 44 to the helicopter's tail rotor servos 48 which control the thrust of the tail rotor 12 through linkages 49. The sensed parameter signals from sensors 31, on lines 32, provide the PFCS and AFCS with the aircraft's angular rate and attitude response to the rotor command signals.

Figure 3:
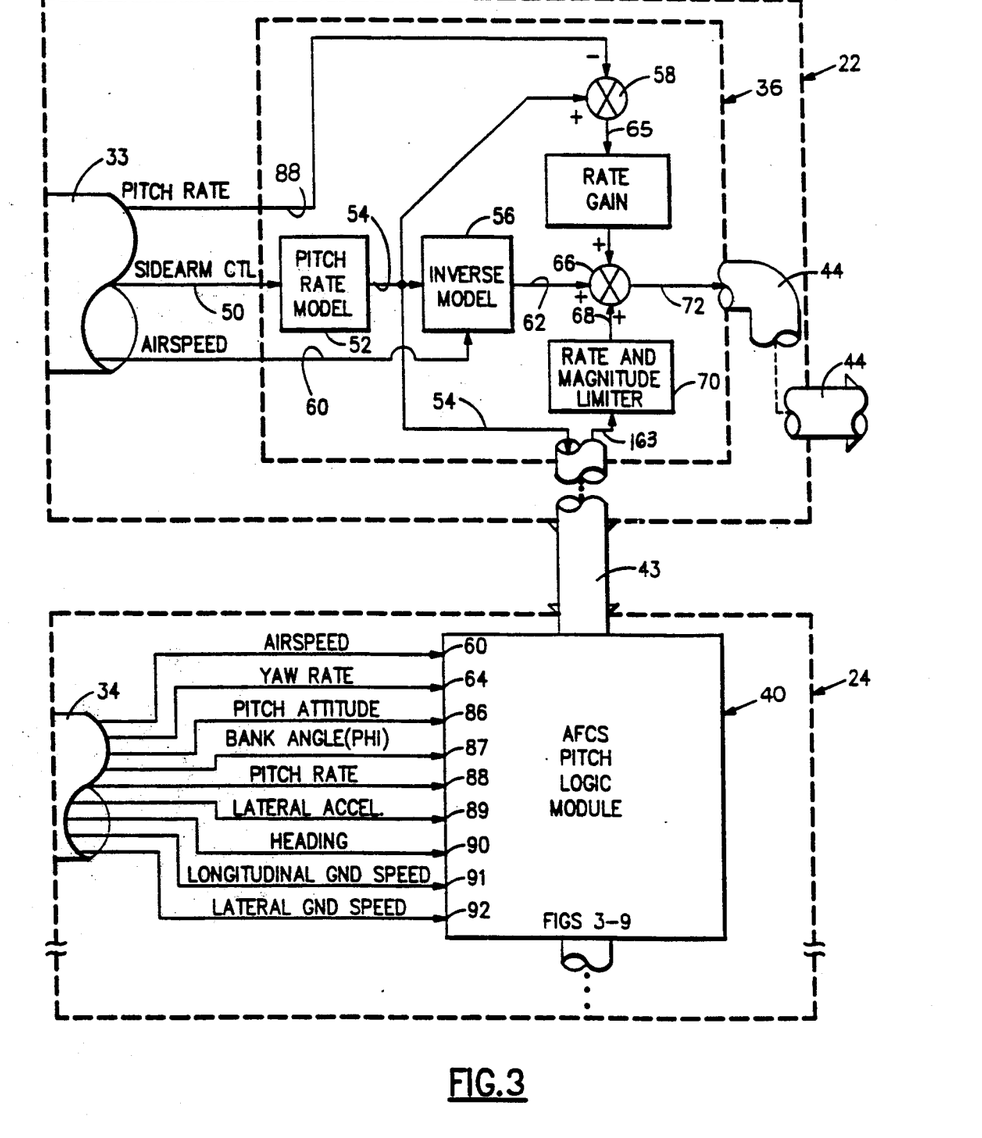
FIG. 3 is a schematic illustration of one portion of the embodiment of FIG. 1.

FIG. 3 is a partial schematic section of FIG. 2, illustrating the functional interconnection of the PFCS 22 and AFCS 24 pitch logic modules 36 and 40, respectfully. The PFCS pitch logic module 36 receives a pitch axis command signal on line 50, provided through trunk lines 33 and lines 30, from the sidearm controller 29 (FIG. 2). In the present embodiment the sidearm controller is a four axis sidearm controller in which the pitch axis command signal is generated by the pilot's imparting a longitudinal force on the sidearm controller. The pitch command signal is presented to the input of pitch rate model circuitry 52 (e.g. a first order lag filter with selected radian/sec signal gain) that provides a desired pitch rate signal on a line 54 indicative of the desired rate of change for the aircraft attitude about the pitch axis. Selection of the pitch rate model order of magnitude is dependant on the dynamics of the aircraft and the pitch response desired.

The desired pitch rate signal on line 54 is presented simultaneously to: the input of a pitch-axis, vehicle inverse model 56, a summing junction 58, and the bus 43 to the AFCS pitch logic module 40. The inverse model 56 receives the aircraft's actual airspeed from sensors 31, through lines 32 and trunk 33, as a sensed airspeed signal on line 60. The inverse model 56 is a Z-transform model, which may be embodied as a first order lead filter with instantaneous voltage gain and time constant characteristics which vary with the magnitude of the sensed airspeed signal on line 60. The cascaded pitch rate model 52 and inverse model 56 provide a feedforward path for the sidearm control signal on line 50.

The feedforward, inverse Z transform model provides the primary control input to the main rotor assembly 11 (FIG. 1) which causes the helicopter 10 (FIG. 1) to pitch at a rate set by a desired pitch rate command signal on a line 62. This desired pitch rate signal represents the main rotor command necessary to achieve the desired pitch-axis rate of change of the aircraft for each pilot commanded maneuver.

The summing function 58 sums the desired pitch rate signal on line 54 (from the pitch rate model 52) with the aircraft's actual pitch rate, received (from sensors 31, through lines 32 and trunk 33) as a sensed pitch rate signal on line 64, to provide a pitch rate error signal on line 65. The rate error signal is amplified in a rate gain stage and presented to one input of a second summing junction 66. The junction 66 also receives the desired pitch rate command signal on line 62 from the inverse model 56, and a pitch rate modifying signal on a line 68 from a rate and magnitude limiter 70. The limiter 70, which receives a nonlimited version of the modifying pitch rate signal on a line 71 (through bus 43) from the AFCS pitch logic module 40, limits the pitch rate modifying signal magnitude and rate of change to predetermined. The resulting sum signal is provided on the output line 72 of the PFCS pitch logic module 36, and presented through the PFCS output trunk lines 44 to the main rotor servos (46, FIG. 1).

The magnitude and rate of change of the pitch rate modifying signal from the AFCS is a function of the aircraft pitch attitude error. The aircraft pitch attitude error is the second of two feedback loops around the main rotor command signal; the first being the pitch rate error signal on line 65. As described in detail hereinafter, the pitch rate modifying signal is a calculated value provided by a model following algorithm within the AFCS, based on the actual aircraft response to the rotor command signal. The pitch rate modifying signal modifies the magnitude and rate of change of the main rotor command signal.

As shown in FIG. 3, in addition to the commanded pitch rate signal received from the PFCS pitch logic module 36 on line 54 (through trunk 43), the AFCS pitch logic module 40 receives the following sensed aircraft parameters through trunk line 34: actual airspeed (line 60), actual yaw rate (line 64), pitch attitude (line 86), bank angle (PHI) (line 87), roll rate (line 88), lateral acceleration (line 89), heading (line 90), longitudinal ground speed (line 91), and lateral ground speed (line 92). The best mode embodiment of the AFCS is as a microprocessor based electronic control system in which the algorithms of the AFCS logic modules (39-42, FIG. 1) reside in executable program listings stored in memory.

Figure 4:
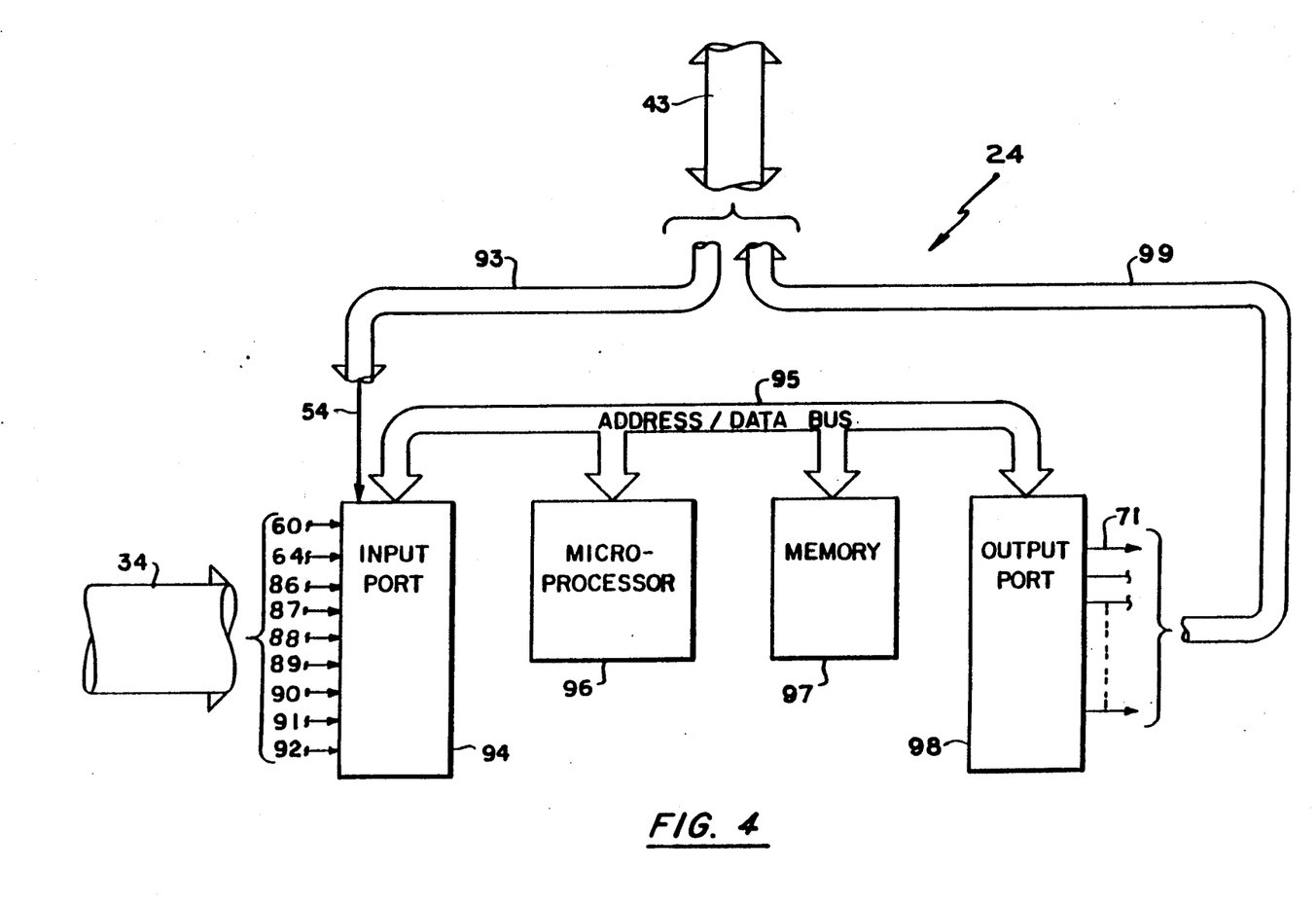
FIG. 4 is a block diagram of one embodiment of one of the system components illustrated in FIG. 2.

FIG. 4, shows the architecture of a microprocessor based AFCS 24. The desired pitch rate signal on line 54 is received from input lines 93 included within the lines 43 interconnecting the AFCS and PFCS. The sensed aircraft parameter signals on lines 60, 64, and 86-92 are received from the AFCS input trunk line 34, at an AFCS input port 94. Depending on the format of the input signals (analog or digital) the input port 94 which may include an analog- to-digital converter, a frequency-to-digital convertor, and such other signal conditioning functions known to those skilled in the art as being required to transform the input signals to digital signal format.

The input port is connected through an address/data bus 95 to a microprocessor 96 (e.g., Intel 80286, Motorola 68020), memory means 97 (including RAM, UV-PROM, EEPROM), and an output port 98. The output port may comprise a digital-to-analog converter, a parallel- to-serial convertor, a discrete output driver, and such other signal conversion functions known to those skilled in the art as being required to transform the AFCS digital signal format to that required by the control system (21, FIG. 1). The output port lines, including the line 71 to the PFCS pitch logic module 36, are presented through lines 99 to the interconnecting lines 43.

Figure 5:
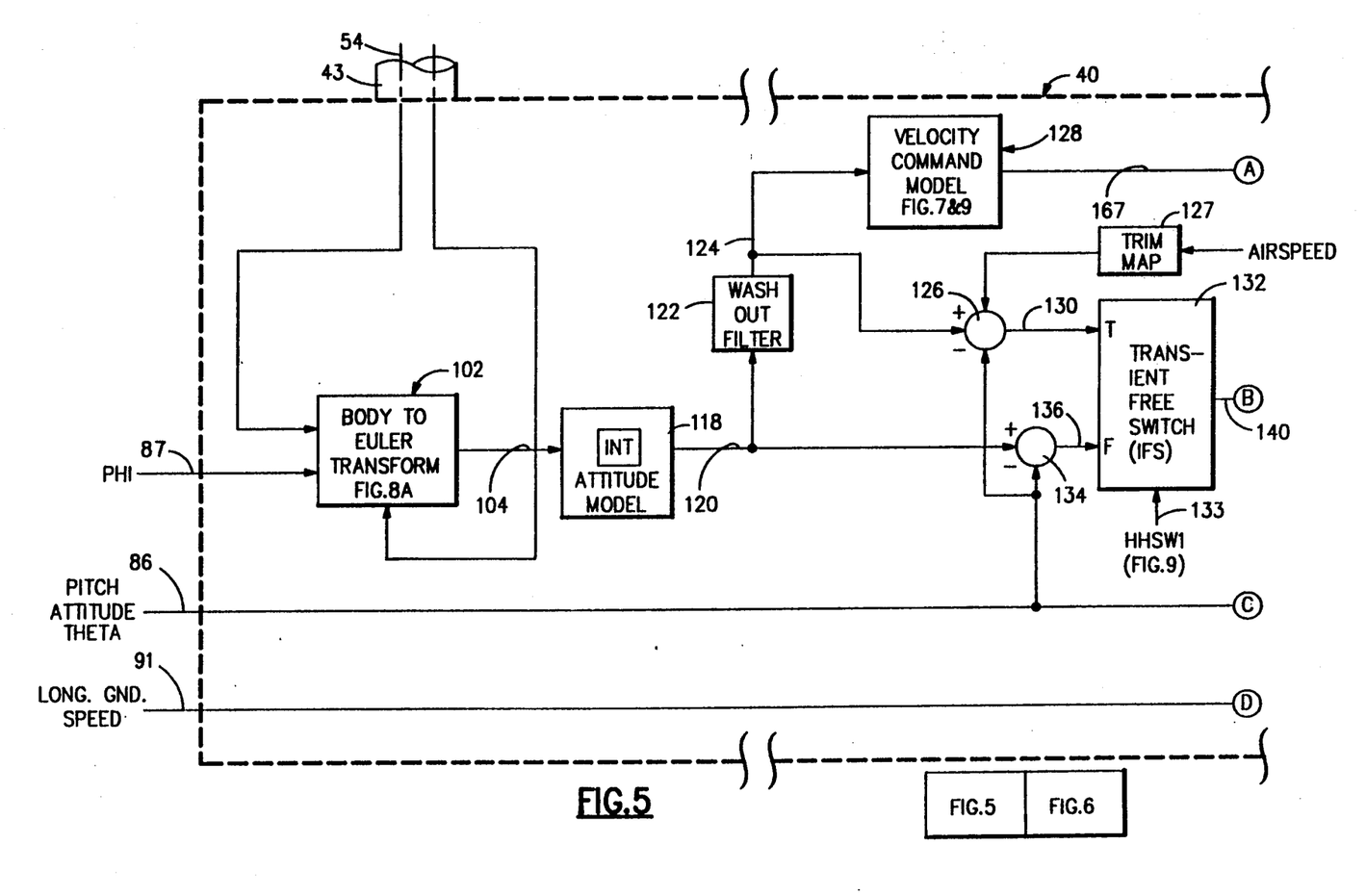
FIG. 5 is a schematic illustration of the functional elements of the embodiment of FIG. 4.
Figure 8A:
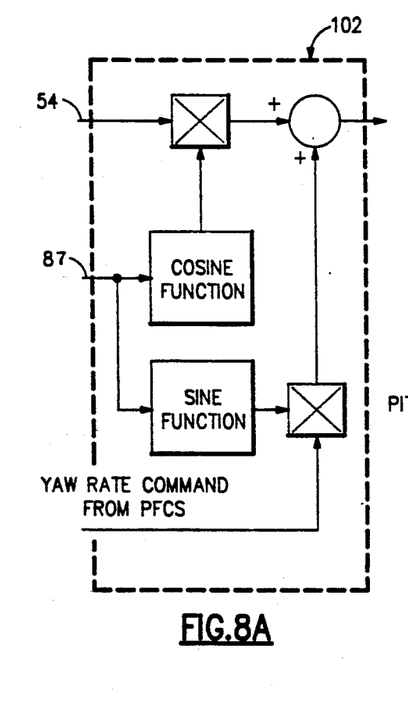
FIG. 8A is a schematic illustration of still further functional details of the embodiment of FIG. 4.

In FIG. 5 is illustrated a block diagram of a portion of the AFCS pitch control logic resident in the memory 97, and which executes in the microprocessor 96. The present invention is also applicable to control of the AFCS roll logic module 41 with only changes to the applicable roll signals. The desired pitch rate command from the PFCS is input on the line 54 to a Body-to-Euler Transformation 102 which also receives the actual vehicle pitch rate, PHI on the line 86. The transformation provides a commanded pitch rate signal on a line 104 that has been transformed from a reference about the aircraft body axes to a reference about inertial axes. In FIG. 8A, is a detailed illustration of the logic of the transform. An explanation of the transform logic operation is not necessary since the operation is apparent from the illustration to one of ordinary skill in the art. Referring back to FIG. 5, the commanded pitch rate signal is input to a pitch attitude model 118 (e.g., an integrator) which integrates over time, and provides a desired pitch attitude signal on a line 120.

The desired pitch attitude signal is input to a washout filter 122 (i.e., derivative/lag filter with a 2 second time constant), which provides a washed out signal on a line 124 to a summer 126, and a velocity command model 128. The summer 126 receives: the pitch attitude signal THETA on the line 86, an attitude bias from a trim map 127, and the signal on the line 124 to provide a washed out error signal on a line 130 to a transient free switch (TFS) 132.

The desired pitch attitude signal on the line 120 is also input to a summing function 134 which receives the actual pitch attitude signal THETA, and provides a pitch attitude error signal on a line 136 to the TFS 132. The TFS operation is controlled by a signal HHSW1 on a line 133 which is a boolean signal indicative of whether or not velocity command mode is engaged. A discussion of how HHSW1 is controlled will be provided hereinafter. If velocity command mode is engaged (i.e., HHSW1=1), the TFS selects the signal on the line 130 which is indicative of the attitude error associated with operating in velocity command mode. Otherwise, the TFS selects the signal on the line 136 which is indicative of attitude error associated with operating in the attitude command mode. The TFS provides a smooth transition of its output signal when the discrete signal HHSW1 changes. That is, rather than instantaneously switching its output signal on a line 140 between the signals on the lines 130,136, the TFS linearly transitions between the two signals when HHSW1 changes state, providing a smooth transition of the TFS output provided on the line 140. An explanation of the velocity command model is now in order.

Figure 7:
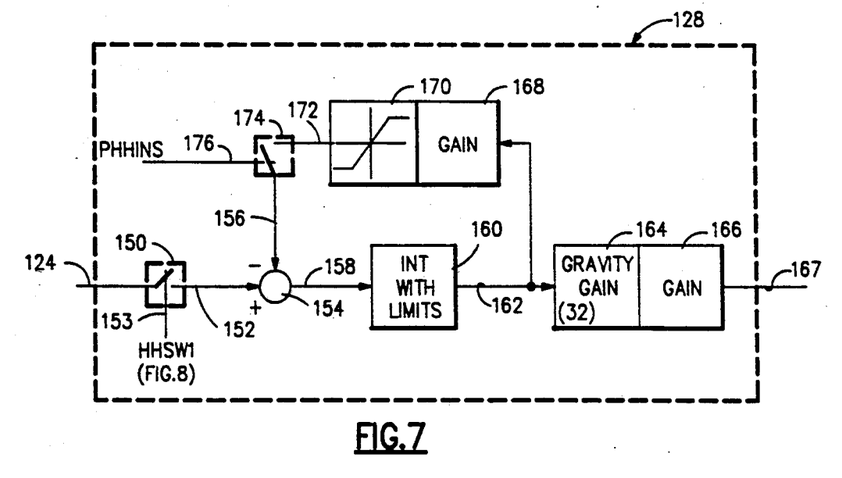
FIG. 7 is a schematic illustration of further functional details of the embodiment of FIG. 4.

In FIG. 7 is an illustration of the velocity command model 128. Within the model, the washed signal on the line 124 is provided to a switch 150 whose position is dependent upon whether velocity command mode is engaged. If velocity command is engaged the switch 150 is placed in the closed position allowing the washed out signal to pass along a line 152 to a summing function 154. Note, when the pilot applies a change in force to the sidearm controller 29 in the direction the pilot desires the aircraft 10 to move, the washed out signal on the line 124 is non-zero. The summing function 154 also receives a feedback signal on a line 156, and provides a difference signal on a line 158 to an integrator with limits 160. The difference signal is integrated over time and an integrated signal is provided on a line 162 to a gravity gain 164. The gravity gain provides a product in units of velocity to a sensitivity gain 166 whose value sets the sensitivity of the model 128. The sensitivity gain provides a velocity command signal on a line 167.

The integrated signal on the line 162 is also input to a feedback gain 168 which provides a signal to a limit function 170. The limit function provides a limited feedback signal on a line 172 which is input to a switch 174 responsive to a discrete signal PHHINS on a line 176. The feedback path (162,172,156) acts to washout the integrator when no force is being imparted on the sidearm controller (i.e., the pilot is requesting zero velocity) to ensure there are no steady state velocity commands. The value of the feedback gain sets the time constant of the first order lag created by providing the feedback path around the integrator 160.

Figure 9:
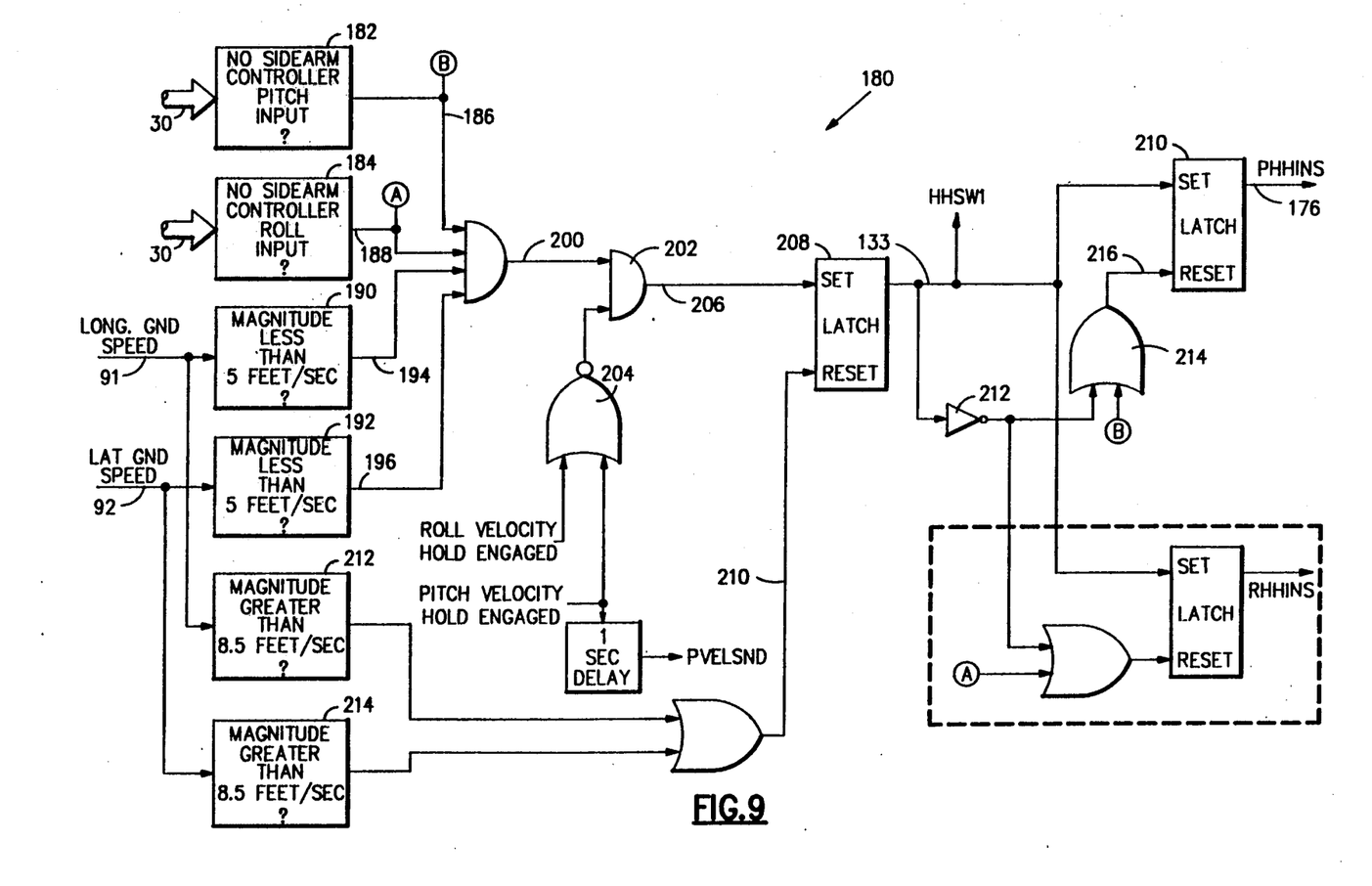
FIG. 9 is a schematic illustration of still further functional details of the embodiment of FIG. 4.

In FIG. 9 is an illustration of control logic 180 for the various discrete signals used for switching and event triggering. The logic receives commands from the sidearm controller 29 via the lines 30. Comparison functions 182,184 each judge the sidearm control commands to determine if the pilot is providing either a pitch command or a roll command. If the pilot is not providing a pitch command, the comparator 182 provides a signal on a line 186 which is set, otherwise the signal is cleared. Comparator 184 operates in a similar manner but judges if a roll command is being input via the sidearm controller. If roll input is not being provided provided the comparator 184 sets a signal on a line 188; otherwise the signal is cleared. Magnitude comparators 190,192 receive the longitudinal ground speed signal and the lateral ground speed signal respectively, and each compares the magnitude to the speeds to a threshold value of 5 feet/sec. If the magnitude of the longitudinal ground speed is less than 5 feet/sec, the comparator 190 sets a signal on a line 194. Similarly, if the magnitude of lateral ground speed is less than 5 feet/sec., comparator 192 sets a signal on a line 194. Each comparator clears its respective output if the magnitude of its input signal exceeds 5 feet/sec.

The signals from comparators 182,184,186 and 192 are all input an AND gate 198 which provides an output on line 200 to a two input AND gate 202. The two input AND gate also receives a signal from a NOR gate 204 which is cleared if either pitch velocity hold or roll velocity hold is engaged. The second AND gate provides a signal on a line 206 to a latch 208. If the signal on the line 206 is set, the output of the latch HHSW1 on the line 133 is set if the reset of the latch on a line 210 is cleared. The latch reset input has priority over the set input. The signal on the line 210 is set if the magnitude of either the longitudinal ground speed or the lateral ground speed is greater than 8.5 feet/sec as judged by comparators 212,214, thus clearing HHSW1 on the line 133. The circuit combination 204,202,208 insures that the velocity command mode cannot be engaged if currently disengaged, while roll or pitch velocity hold is engaged.

The velocity command engage signal HHSW1 on the line 133 is input to a second latch 210 and an inverter 211. If HHSW1 is set, the output of the inverter is cleared and input to an OR gate 213 along with the signal on the line 186 from the pitch input comparator 182. If there is no sidearm controller pitch input or the velocity command mode is not engaged (HHSW1=0), the OR gate 214 provides an output signal on a line 216 which is set, which in turn resets the latch clearing the latch output signal PHHINS on the line. With the understanding of how the various discrete signals are controlled, the discussion can now return to FIGS. 5-6.

Figure 6:
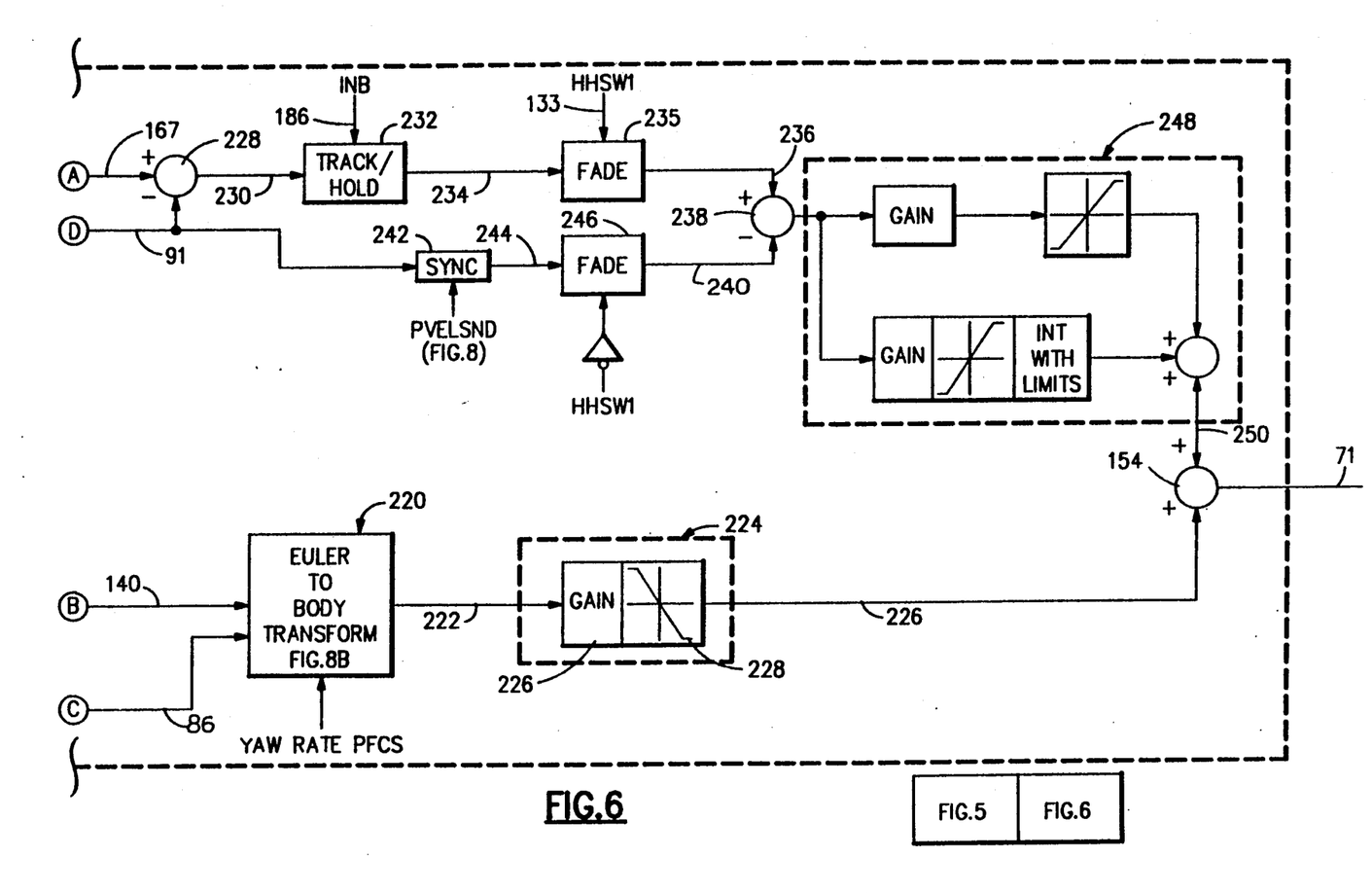
FIG. 6 is a companion schematic illustration of FIG. 5.

The TF switch 132 provides the signal on the line 140 to a Euler-to-Body transform 220 which transforms the selected error signal on the line 140 which is in terms of Euler axes, back to aircraft body axes. The operation of the transform involves straight mathematics as shown. The transform 220 provides a transformed error signal on a line 222 to a proportional compensator 224 having a gain function 226 and a limiting function 228 which are cascaded to provide a signal on a line 226.

Figure 8B:
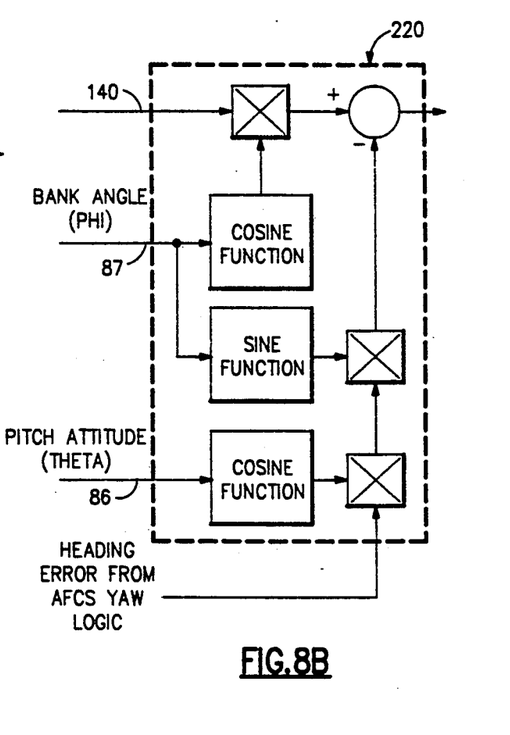
FIG. 8B is a schematic illustration of still further functional details of the embodiment of FIG. 4.

The velocity command model 128 provides its output signal on the line 167 to a summing function 228 which also receives the longitudinal ground speed signal on the line 91. The summing function 228 provides a signal on a line 230 which is indicative of the longitudinal ground speed error, i.e., it represents the difference between the output signal from the velocity command model and the actual longitudinal ground speed. The longitudinal ground speed error is input to a track/hold function 232 which is controlled by HHSW1 on the line 133. When HHSW1 is cleared the function operates in track mode allowing the signal on the line 230 to pass to 232, and when set the function holds the past value on the output line. The track/hold function in used to smooth the transition in and out of velocity command mode by holding its output signal on a line 234 constant while a fade function 235 fades the longitudinal speed error signal out when velocity command mode is disengaged (i.e., HHSW1 transitions from set to clear). The fade function allows for a smooth transition on the fade output signal on a line 236 by fading the signal on the line in and out over a period of time (e.g., 3 seconds) as the system transitions in and out velocity command, depending upon the conditions shown in FIG. 8. The fade function 235 provides the signal on the line 236 to a summing function 238, which also receives a signal on a line 240.

The longitudinal ground speed signal on the line 91 is also input to a synchronizer 242 which is responsive to the discrete signal PVSELND which is a delayed version of the pitch attitude hold engaged signal. PVELSND is set when pitch velocity hold is engaged, and conversely it is cleared when pitch velocity hold is disengaged. When PVELSND is cleared the synchronizer 242 continuously stores the value of the longitudinal ground speed signal on the line 91, and provides an output signal on a line 244 which is equal to zero. When PVELSND transitions from clear to set, indicating that pitch velocity hold has been engaged, the synchronizer begins to provide a signal on the line 244 which is indicative of the difference between the current value of the signal on the line 91, and stored value within the synchronizer, which represents the signal on the line when PVELSND transitioned from clear to set. The synchronized signal is input to a fade function 246 whose operation is controlled by the inverted version of the velocity command mode enable signal HHSW1. Therefore, the fade function 246 fades in the signal on the line when velocity command mode is disengaged (i.e., HHSW1 transitions from set to clear), and fades out the signal on the line 244 upon engaging the velocity command mode.

The summing function takes the difference of the signals on lines 236,240 and provides a difference signal to a proportional and integral compensator 248. The compensator provides a signal on a line 250 which is summed with the signal on the line 226 by the summing function 154 to provide the nonlimited pitch modifying command signal on the line 71.

The present invention may be incorporated with a hover hold system an example of which is co-pending application Ser. No. 07/518,593 filed May 3, 1990, entitled "Hover Position Hold System for Rotary Winged Aircraft". This allows the present invention to act as a bias to the hover hold input signal to the mixer, where the bias amount is indicative of the new desired aircraft hover position.

While the present invention has been illustrated in an exemplary embodiment of a microprocessor based electronic control system, one skilled in the art will appreciate that the present invention can be implemented in electronic hardware without the use of a microprocessor. Furthermore, it should be understood that the partitioning of the tasks between the PFCS and the AFCS for the purposes of the present invention is not necessary, rather the partitioning represents the system design conventionally done for a flight control system due to the reliability concerns of placing the complete flight control system in a single electronic package. It should also be noted that the present invention is clearly not limited to attack helicopters, but rather the present invention has applicability to all rotary winged aircraft which seek the advantages of a velocity command mode while operating at low aircraft ground speeds.

Although the present invention has been shown and described with respect to a best mode embodiment thereof, it should be understood by those skilled in the art that various other changes, omissions and additions to the form and detail thereof, may be made therein without departing from the spirit and scope of the present invention.

We claim:

1. A helicopter flight control system of the type having a plurality of sensors which provides: rate signals indicative of the helicopter's pitch and roll rates of change, attitude signals indicative actual bank angle and pitch attitude, and a signal indicative of actual ground speed; a sidearm controller provides a control input signal value indicative of desired ground speed to the system which controls ground speed in response to the control input signal by providing a command signal to the helicopter's main rotor, the control system comprising:

means for providing, for each value of the control input signal, a corresponding signal value indicative of the helicopter desired rate of change about the pitch and roll axes of the helicopter;

a feedforward path including inverse model means for providing for each said desired rate of change signal value a feedforward set point signal value indicative of the command to the main rotor required for the helicopter to fly at the desired ground speed;

a rate feedback path including means for computing a difference value between said desired rate of change signal value and the corresponding sensed rate of change signal value, and for providing a rate of change error signal value indicative of the difference;

an attitude feedback path comprising:

means for integrating said desired rate of change signal value to provide a desired attitude signal value;

means for computing a difference value between said desired attitude signal value and the corresponding sensed attitude signal value, and for providing an attitude error signal value indicative of the difference;

means, having a derivative lag filter, for filtering said desired attitude signal value to provide a washed out signal value;

velocity model means, for providing for each value of said washed out signal, a desired ground speed command signal value indicative of the desired helicopter ground speed;

means for computing a difference value between said desired ground speed command signal value and the sensed ground speed signal value, to provide a ground speed error signal value indicative of the difference;

means for summing said ground speed error signal value and said attitude error signal value to provide a command modifying signal;

means for summing said command modifying signal value, said rate error signal value, and said feedforward signal value to provide a command signal; and means for outputting said command signal to the main rotor.

2. A helicopter flight control system of the type having a plurality of sensors which provide: rate signals indicative of the helicopter's pitch and roll rates of change, attitude signals indicative of actual bank angle and pitch attitude, and a ground speed signal; a controller provides a control input signal value indicative of desired ground speed to the system which controls the helicopter's ground speed by providing a command signal to the helicopter's main rotor, the control system comprising:

means for providing, for each value of the control input signal, a corresponding signal value indicative of the helicopter desired rate of change about the pitch and roll axes of the helicopter;

inverse model means for providing for each said desired rate of change signal value a feedforward set point signal value indicative of the command to the main rotor required for the helicopter to achieve said desired rate of change signal value;

means for computing a difference value between said desired rate of change signal value and the corresponding sensed rate of change signal value, and for providing a rate of change error signal value indicative of the difference;

means for transforming said desired rate of change signal value from its basis with respect to helicopter body axes to a new basis with respect to Euler inertial axes, and for providing a transformed desired rate of change signal value indicative thereof;

means for integrating said transformed desired rate of change signal value to provide a desired attitude signal value;

means for computing a difference value between said desired attitude signal value and the corresponding sensed attitude signal value, and for providing an attitude error signal value indicative of the difference;

means for re-transforming said attitude error signal value back to the basis with respect to the helicopter body axes, and for providing a re-transformed attitude error signal value indicative thereof;

means, having a derivative lag filter, for filtering said desired attitude signal value to provide a washed out signal value;

velocity model means, for providing for each value of said washed out signal, a desired ground speed command signal value indicative of the desired helicopter ground speed;

means for computing a difference value between said desired ground speed command signal value and the second ground speed signal value, to provide a ground speed error signal value indicative of the difference;

means for summing said ground speed error signal value and said re-transformed attitude error signal value to provide a command modifying signal;

means for summing said command modifying signal value, said rate error signal value, and said feedforward signal value to provide a command signal; and means for outputting said command signal to the main rotor.

3. The system of claim 2, wherein said velocity model means comprises:

means for computing a difference value between said washed out signal and a forcing signal to provide an error signal indicative of the difference value;

means for integrating said error signal value to provide said desired ground speed command signal;

feed back means, for multiplying said desired ground speed signal by a gain value, and for limiting the gain multiplied value of said desired ground speed command signal, and for providing a feed back signal value indicative of the limited value; and switch means, for setting said forcing signal equal to said feed back signal value when the magnitude of either the lateral or the longitudinal ground speed signals exceeds a first threshold value, and for setting said forcing signal equal to zero when both the lateral and longitudinal ground speed signals are less than a second threshold value.

4. The system of claim 3, wherein said inverse model means includes a lead filter of at least first order which provides said feedforward set point signal value.

5. The system of claim 4, wherein said means for re-transforming includes a proportional and integral compensator for providing said transformed heading error signal value.

6. The system of claim 3, wherein said means for providing includes a first order lag filter which is responsive to each value of the control input signal for providing said desired rate of change signal value; and said inverse model means includes a lead filter responsive to each value of said desired rate of change signal for providing said feedforward set point signal value.

7. The system of claim 1, wherein said attitude feedback path further comprises:

means for transforming said desired rate of change signal value from its basis with respect to helicopter body axes to a new basis with respect to Euler inertial axes; and means for re-transforming said attitude error signal value back to the basis with respect to the helicopter body axes.

8. The system of claim 7, wherein said velocity model means further comprises:

an integrator which receives an input signal value and provides said desired velocity command signal value;

switch means for providing a forcing signal, by setting said forcing signal equal to a signal indicative of said desired velocity command signal value when the magnitude of either the lateral or the longitudinal ground speed signals exceeds a first threshold value, and for setting said forcing signal equal to zero when both the lateral and longitudinal ground speed signals are less than a second threshold value; and means for providing said input signal by computing a difference value between said washed out signal and said forcing signal and for providing said input signal with a value indicative of the difference.

9. The system of claim 8, wherein said means for providing includes a first order lag filter which is responsive to each value of the control input signal for providing said desired rate of change signal value; and said inverse model means includes a lead filter responsive to each value of said desired rate of change signal for providing said feedforward set point signal value.

10. The system of claim 7, wherein said velocity model means further comprises:

an integrator which receives an input signal value and provides said desired velocity command signal value; and means for providing said input signal by computing a difference value between said washed out signal and said desired velocity command signal value, and for providing said input signal with a value indicative of the difference.

* * * * *